United States Patent
Gillis

(10) Patent No.: US 7,691,096 B2
(45) Date of Patent: Apr. 6, 2010

(54) ANGLED MEDICAL CONNECTOR WITH HEIGHT COMPENSATOR

(75) Inventor: Gary A. Gillis, Ann Arbor, MI (US)

(73) Assignee: Centurion Medical Products Corporation, Williamston, MI (US)

( * ) Notice: Subject to any disclaimer, the term of this patent is extended or adjusted under 35 U.S.C. 154(b) by 901 days.

(21) Appl. No.: 11/261,054

(22) Filed: Oct. 28, 2005

(65) Prior Publication Data

US 2007/0106265 A1    May 10, 2007

(51) Int. Cl.
*A61M 25/18* (2006.01)
(52) U.S. Cl. ..................................... 604/535
(58) Field of Classification Search ................ 604/174, 604/533, 534, 539, 535
See application file for complete search history.

(56) References Cited

U.S. PATENT DOCUMENTS

| | | | | |
|---|---|---|---|---|
| 4,164,943 A | * | 8/1979 | Hill et al. | 604/174 |
| 4,435,174 A | * | 3/1984 | Redmond et al. | 604/174 |
| 4,578,057 A | | 3/1986 | Sussman | |
| 4,878,897 A | * | 11/1989 | Katzin | 604/86 |
| 4,997,421 A | | 3/1991 | Palsrok et al. | |
| 5,054,723 A | * | 10/1991 | Arnold | 248/65 |
| 5,125,915 A | * | 6/1992 | Berry et al. | 604/533 |
| 5,192,273 A | * | 3/1993 | Bierman | 604/174 |
| 5,354,282 A | * | 10/1994 | Bierman | 604/180 |
| 5,456,671 A | * | 10/1995 | Bierman | 604/180 |
| 5,626,565 A | * | 5/1997 | Landis et al. | 604/174 |
| 5,722,959 A | * | 3/1998 | Bierman | 604/174 |
| 5,800,402 A | * | 9/1998 | Bierman | 604/180 |
| 6,231,548 B1 | | 5/2001 | Bassett | |
| 2002/0188255 A1 | * | 12/2002 | Bierman et al. | 604/174 |
| 2005/0027258 A1 | | 2/2005 | Bierman et al. | |

* cited by examiner

*Primary Examiner*—Nicholas D Lucchesi
*Assistant Examiner*—Aarti B Berdichevsky
(74) *Attorney, Agent, or Firm*—Fildes & Outland, P.C.

(57) ABSTRACT

A medical connector for connecting medical tubing to a catheter includes a connector body and a height compensating foot. The connector body has a catheter leg adapted to connect to the catheter, a medical tubing leg adapted to connect to the medical tubing, and an angular bend intermediate the legs. The height compensating foot is attached to the catheter leg and extends outwardly therefrom at an angle to prevent the connector from rocking and tubing from overhanging a patient's knuckles when connected to the catheter inserted in a patient.

20 Claims, 4 Drawing Sheets

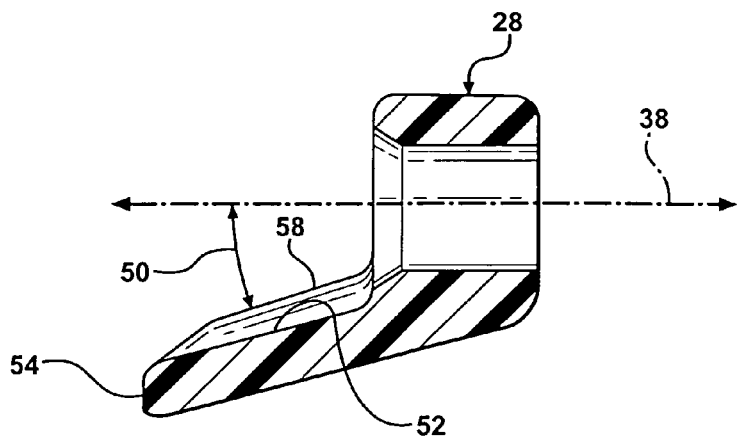
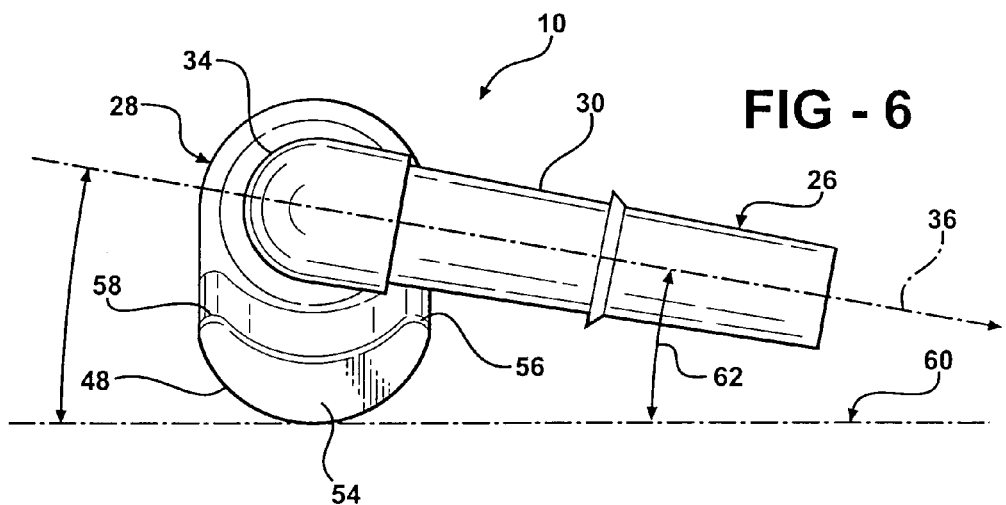
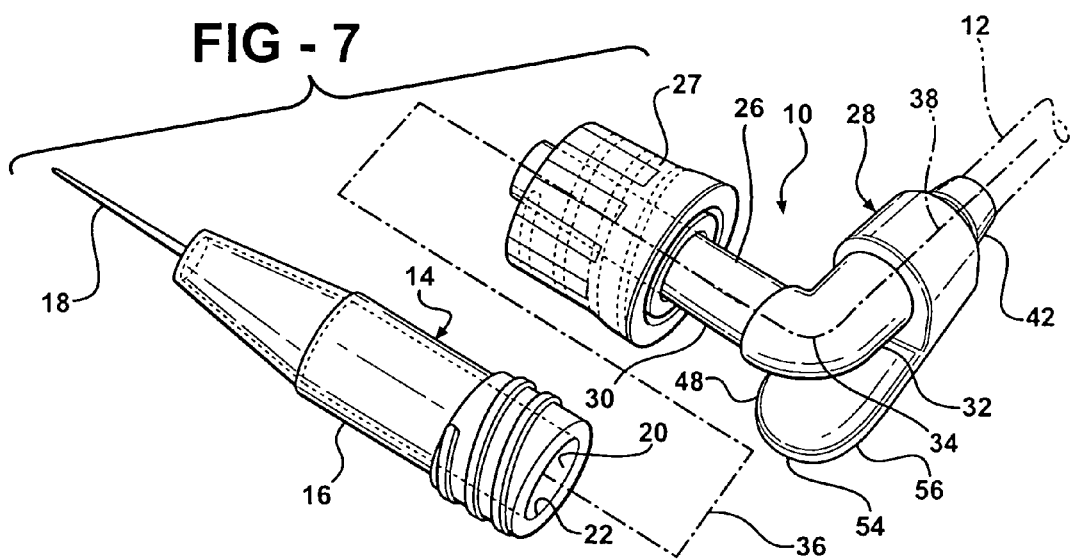

ANGLED MEDICAL CONNECTOR WITH HEIGHT COMPENSATOR

TECHNICAL FIELD

This invention relates to medical connectors and more specifically to an angled medical connector that compensates for the difference in height between a catheter lumen and an associated connector disposed on a patient.

BACKGROUND OF THE INVENTION

In the medical and surgical fields, intravenous (IV) fluids are generally administered to a patient through a catheter inserted into a vein of the patient. The catheter is typically coupled to an IV connector, which is connected by IV tubing to a container of IV fluid.

Generally the catheter includes an insertion end and a connecting end configured as a female fitting having a diameter substantially larger than the catheter itself. A cooperating connector has a male fitting portion adapted to mate with the female fitting. The female and male fittings are commonly configured as luer lock type fittings. As luer fittings, the male portion of the IV connector has a precise tapered outer surface, and the catheter's aperture has a similarly tapered female bore. When assembled, the tapered male and female surfaces engage in a slip type interference fit to frictionally fit the catheter and connector together. A fastening means is provided to lock the catheter and connector together.

By design, the threaded collar or female catheter has a larger outside diameter than the male connector, catheter and associated medical tubing connected thereby to the catheter. Problematically however, the relatively larger diameter of the connector portion causes the assembled catheter and connector to teeter, or rock, back and forth about the centerline of the connector. This teetering effect can cause patient discomfort, and some loosening of dressings holding the catheter in place, when the catheter is inserted in a patient.

Additionally, this teetering or rocking about the connector can cause in-and-out movement of the catheter tip causing vessel wall damage, or even full infiltration of the catheter tip through the vessel wall.

SUMMARY OF THE INVENTION

The present invention provides an angled medical connector for connecting medical tubing to a catheter. The connector includes a connector body and a height compensating foot mounted thereon. The height compensating foot compensates for the larger diameter of the catheter connector and prevents rocking of the connector when connected to a catheter inserted in a patient.

Further, the angled medical connector of the present invention overcomes deficiencies of conventional fittings and tubing. When an IV catheter is inserted on the back of the hand, conventional fittings and tubing connected to the catheter hang over the knuckles of the hand. It is common that the fittings/tubing may overhang between a half inch and one and a half inches. This configuration has a high risk of catheter dislodgement, blood vessel damage, dressing rip up, etc. due to snagging or pulling on the overhanging fittings/tubing. The present angled connector reduces the risk of these occurrences by routing the fittings and tubing away from the knuckles on a hand, preventing knuckle overhang. The present invention also eliminates the need to use rigidizing arm boards and the like.

In an exemplary embodiment of the present invention a medical connector includes a connector body and a height compensating foot. The connector body has an elongated hollow catheter leg having a first end portion adapted to detachably connect to a catheter. A first axis extends centrally through the hollow portion of the catheter leg. The connector body also has an elongated hollow medical tubing leg having a second end portion adapted to connect to medical tubing. A second axis extends centrally through the hollow portion of the medical tubing leg. The connector body further includes an angular bend intermediate the catheter leg and medical tubing leg wherein the first and second axes intersect. The height compensating foot is attached to the medical tubing leg and extends outwardly therefrom at an angle to prevent rocking about the first and second axis when connected to the catheter inserted in a patient.

In another exemplary embodiment of the medical connector, the height compensating foot is rotatable about the second axis to provide a plurality of mounting dispositions.

In an alternative embodiment the medical tubing leg of the connector has an annular portion with a recessed outer surface adjacent the second end portion. The height compensating foot has a hollow circular collar sized to rotatably fit around the outer surface of the annular portion. Additionally the height compensating foot has a foot support member projecting from the collar to form an acute angle relative to the second axis. The foot support member is bounded by first and second edges. Herein, the catheter leg abuts against the first edge when the medical connector is in a first mounting position. Alternatively, the catheter leg abuts against the second edge when the medical connector is in a second mounting position.

These and other features and advantages of the invention will be more fully understood from the following detailed description of the invention taken together with the accompanying drawings.

BRIEF DESCRIPTION OF THE DRAWINGS

In the drawings:

FIG. 5 is a side cross sectional view of the height compensating foot of FIG. 4 taken along the line 5-5;

FIG. 6 is a front view of the medical connector of FIG. 1 in a first mounting position;

FIG. 7 is an exploded perspective view of the medical connector of FIG. 1;

DETAILED DESCRIPTION OF THE INVENTION

Figure 1:
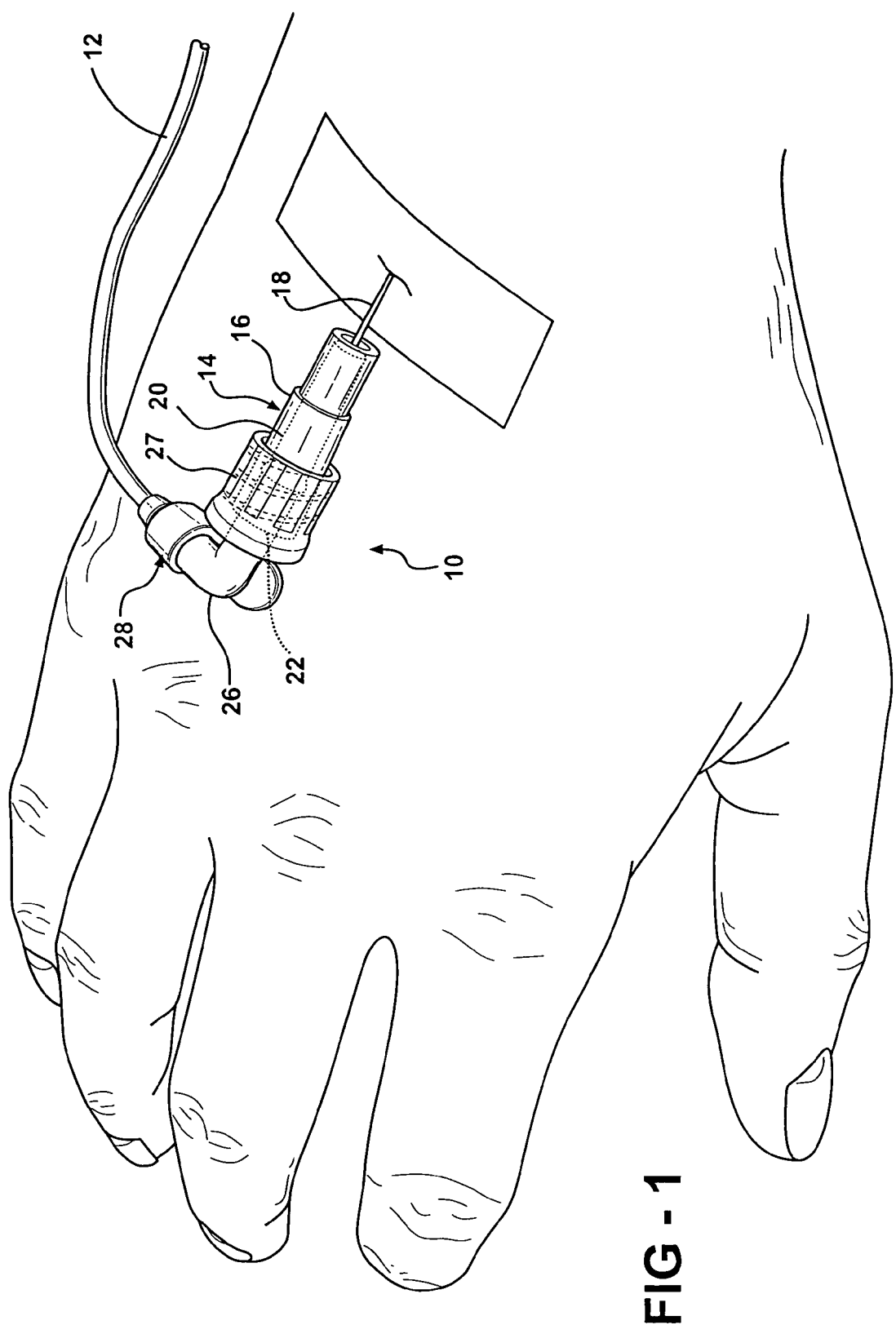
FIG. 1 is an environmental perspective view of an exemplary embodiment of an angled medical connector connecting IV tubing to a catheter on a patient in accordance with the present invention.

Referring now to FIG. 1, numeral 10 generally indicates an exemplary embodiment of an angled medical connector in accordance with the present invention. Medical connector 10 is shown connecting IV tubing 12 to catheter 14, which is inserted into a patient.

The IV tubing 12 is typically connected to a container of IV fluid, which is generally positioned to allow the IV fluid to be fed through the tubing 12, connector 10 and catheter 14 into the patient. Although IV tubing is illustrated herein, one skilled in the art will recognize that the connector 10 may be utilized with other types of medical tubing, such as surgical drainage tubes, feeding tubes, or the like.

The catheter 14 is hollow and includes a hub 16 and a sheath 18 fluidly connected to the front end of the hub 16. The sheath 18 of the catheter 14 is typically inserted as is known into a vein of the patient and used to administer IV fluids or the like. The interior surface 20 of the hub 16 has a conical shape, which is precisely tapered outwardly toward aperture 22 formed in the rear end of the hub. The aperture 22 and interior surface 20 of the hub 16 form a female luer type fitting adapted to mate with the connector 10.

Connector 10 includes a generally right angled connector body 26, though the connector body 26 may be angled at an angle greater or smaller than 90 degrees. A height compensating foot 28 is mounted on one leg of the connector body 26. The height compensating foot 28 may be rotatably mounted on the connector body 26, or alternatively may be snap fittable on the connector body or even integral with the connector body. As will be explained in greater detail hereinafter, the height compensating foot 28 advantageously serves to compensate for the larger diameter of the catheter hub 16, or threaded collar 27 for mating with the catheter hub 16, and prevents the connector body 26 from a rocking or teetering effect when connected to catheter hub 16. Additionally, the height compensating foot 28 supports the connector body 26 at an incline that is optimally comfortable to a patient when connected to hub 16.

Figure 2:
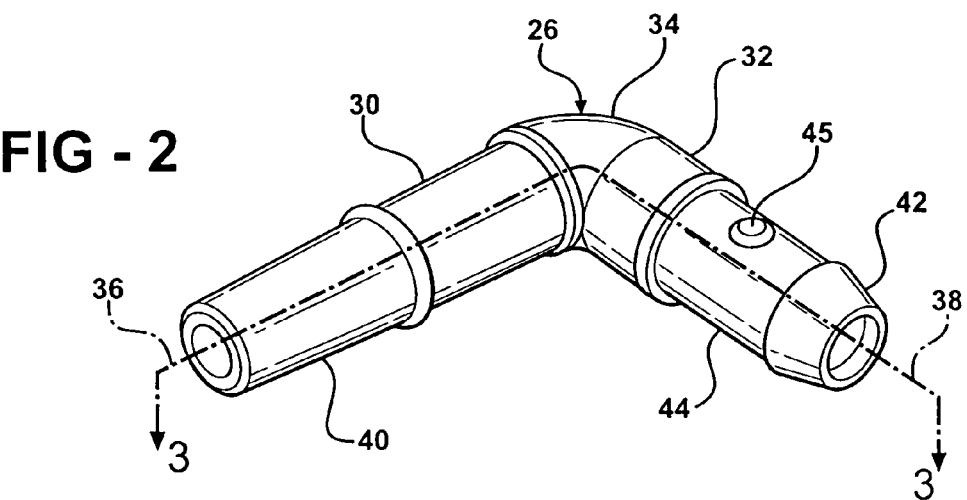
FIG. 2 is a perspective view of the connector body of FIG. 1.
Figure 3:
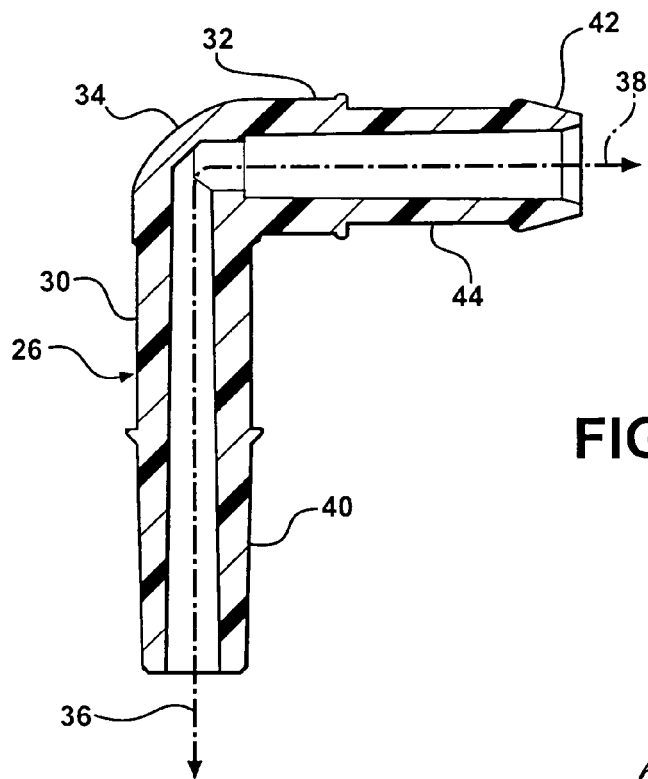
FIG. 3 is a side cross sectional view of the connector body of FIG. 2.

Referring to FIGS. 2 and 3, the connector body 26 has an elongated hollow catheter leg 30 and an elongated hollow medical tubing leg 32 integrally connected to a right angular bend 34 intermediate the legs 30, 32. A first axis 36 and a second axis 38 extend centrally through the hollow portions of the catheter leg 30 and the medical tubing leg 32 respectively to intersect within the angular bend 34.

The catheter leg 30 includes a first end portion 40 adapted to detachably connect to the catheter 14. The first end portion 40 may be configured as a male luer type fitting. The male luer fitting of the connector body 26 is sized to mate with the female luer fitting of the catheter hub 16 to form a fluid tight friction seal therebetween. Though this embodiment describes connector body 26 as having a male lure type fitting, it is within the scope of this invention to utilize other configurations to connect to the catheter hub 16.

Medical tubing leg 32 includes a second end portion 42 adapted to connect to the medical tubing 12, which may be a solvent wipe taper allowing for solvent wiping to prevent solvent etching. An annular portion 44 is formed in the outer surface of the medical tubing leg 32 adjacent the second end portion 42. The annular portion 44 has a surface that is sized to rotatably receive and capture the height compensating foot 28. The surface may be recessed, or may be raised on one or both sides, to capture the foot 28. The medical tubing leg 32 may also include a friction bump 45 adapted to contact the height compensating foot 28 for restraining movement of the height compensating foot about the medical tubing leg.

Figure 4:
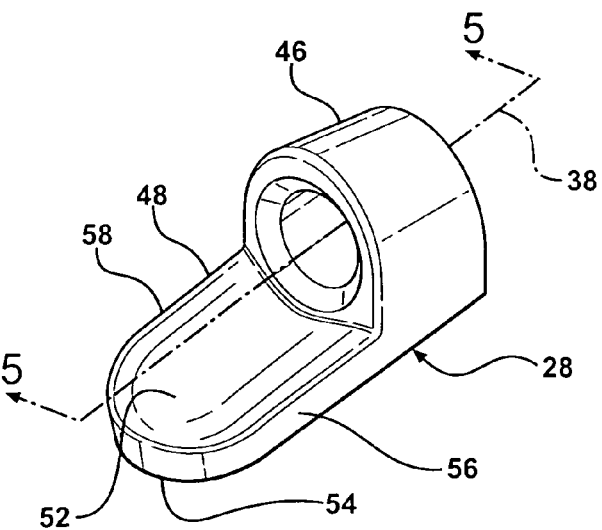
FIG. 4 is a perspective view of the height compensating foot of FIG. 1.

Referring to FIGS. 4 and 5, the height compensating foot 28 may include a hollow circular collar 46 sized to rotatably fit around annular portion 44 to secure the height compensating foot 28 therein. The height compensating foot 28 may alternatively be a split collar or other similarly suitable collar design. Further, the height compensating foot 28 may engage the medical tubing leg 32 anywhere between the angular bend 34 and the second end portion 42. A foot support member 48 projects from the collar 46 to form an acute angle 50 relative to the second axis 38. The foot support member 48 may project in the direction of the angular bend 34. The support member 48 has an inner surface 52, which is bounded by a rounded distal end 54 and first and second edges 56 and 58.

Figure 8:
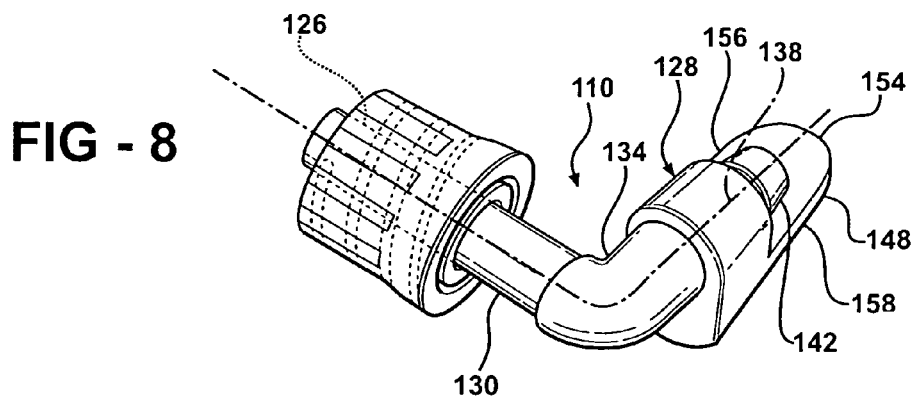
FIG. 8 is a perspective view of an alternative embodiment of an angled medical connector in accordance with the present invention.

Alternatively, in a separate embodiment shown in FIG. 8, the foot support member 148 may project in the direction of the second end portion 142.

Figure 10:
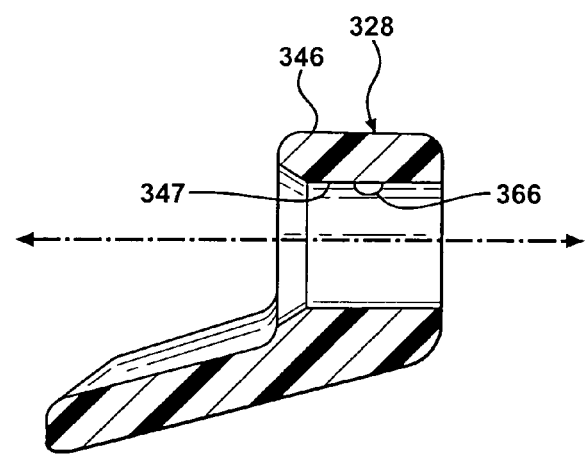
FIG. 10 is a side cross sectional view of an another alternative embodiment of a height compensating foot in accordance with the present invention.
Figure 11:
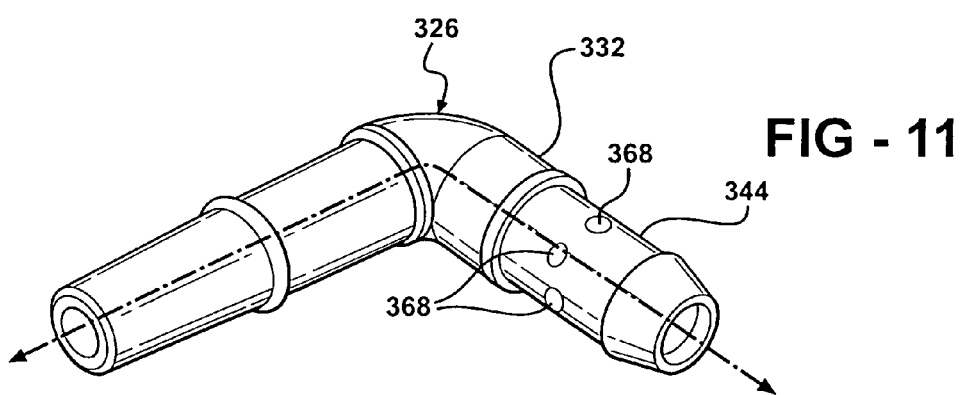
FIG. 11 is a perspective view of a connector body corresponding to the height compensating foot of FIG. 10.

Turning to FIGS. 10 and 11, in yet another embodiment, a height compensating foot 328 and medical tubing leg 332 of a connector body 326 in accordance with the present invention may include a detent arrangement for indexing the foot 328 in positions about the medical tubing leg 332. For example, the height compensating foot 328 may include a raised portion 366, such as a ball, on an inner surface 347 of the collar 346. The medical tubing leg 332 may then include a plurality of recesses 368 on an annular portion 344 thereof. The raised portion 366 and recesses 368 cooperate to form the detent arrangement. It should be understood, however, that the detent arrangement could be reversed. In other words, the foot 328 could include the recesses and the medical tubing leg 332 could include the ball.

Referring now to FIGS. 6 and 7, during operation the medical connector 10 is inserted into the larger diameter catheter 14 to deliver IV fluid to a patient or alternatively to drain fluid from the patient. The connector body 26 and height compensating foot 28 may be positioned in either one of a first mounting position (as illustrated in FIG. 1) or a second mounting position (as illustrated in FIG. 7), or in any position therebetween. With the height compensating foot 28 so positioned, the foot support member 48 of height compensating foot 28 may rest on a support surface such as a surface of the patient, best seen in FIG. 1, to support the medical tubing leg 32 and angular bend 34 of the connector body 26 off of patient skin surface 60. This prevents the assembled catheter 14 and connector 10 from teetering or rocking back and forth about the second axis 38, which extends through the medical tubing leg 32. Additionally, the medical tubing leg 32, extending at a right angle to the catheter leg 30, prevents rocking about the first axis 36, which passes through the catheter leg 30. In other words, when connected in or between the first and second mounting positions, connector 10 will not rock or teeter about either of the first or second axes 36, 38 thereby preventing discomfort and in-and-out catheter tip movement which causes vessel wall damage.

Moreover, the height compensating foot 28 raises the angular bend 34 of the connector body 26 to position the catheter leg 30 at an angle of incline 62 of approximately between 5-30 degrees relative to the patient surface 60 or other support surface. The angle of incline 62 prevents the sheath 18 of the catheter 14 from being tilted upwards against the vein into which it is inserted, thus further relieving discomfort and stress to the patient.

Figure 9:
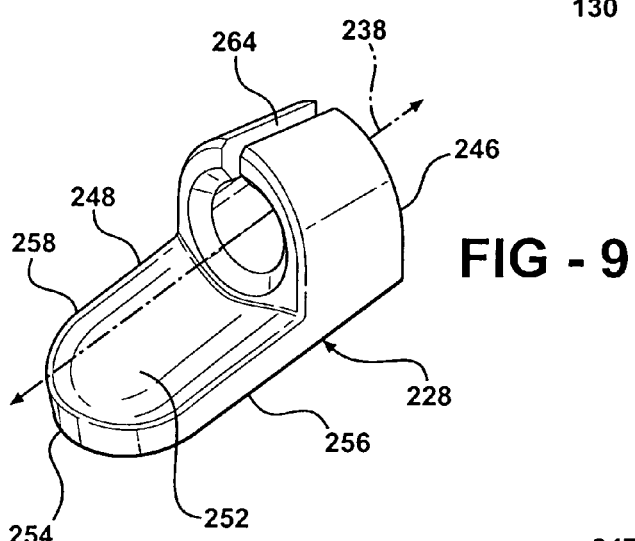
FIG. 9 is a perspective view of an alternative embodiment of a height compensating foot in accordance with the present invention.

Turning to FIG. 9, in an alternative embodiment, a height compensating foot 228 in accordance with the present invention may include a slot 264 in a collar 246 of the foot 228 such that collar is a split collar. This allows the height compensating foot 228 to be snap fittable onto a leg of a connector body of the present invention.

Although the invention has been described by reference to specific embodiments, it should be understood that numerous changes may be made within the spirit and scope of the inventive concepts described. Accordingly, it is intended that the invention not be limited to the described embodiments, but that it have the full scope defined by the language of the following claims.

What is claimed is:

1. A medical connector for connecting medical tubing and a catheter inserted into a patient, the connector comprising:
   a connector body having:
      an elongated hollow catheter leg having a first end portion adapted to detachably connect to said catheter and a first axis extending centrally through said hollow portion of said catheter leg;
      an elongated hollow medical tubing leg having a second end portion adapted to connect to said medical tubing and a second axis extending centrally through said hollow portion of said tubing leg; and
      an angular bend intermediate said catheter leg and medical tubing leg wherein said first and second axes intersect; and
   a height compensating foot on said medical tubing leg and extending outwardly therefrom at an angle to prevent rocking about said first and second axis when connected to a catheter inserted in a patient, said height compensating foot including a collar rotatably mountable on said medical tubing leg and a cantilevered foot support member extending from said collar.

2. The medical connector of claim 1 wherein said angular bend of said connector body comprises generally a 90 degree angular bend.

3. The medical connector of claim 1 wherein said first end portion comprises a tapered male luer fitting.

4. The medical connector of claim 1 wherein said height compensating foot engages said medical tubing leg between said angular bend and said second end portion.

5. The medical connector of claim 1 wherein said height compensating foot is snap fittable on said medical tubing leg.

6. The medical connector of claim 1 wherein said height compensating foot is integral with said connector body.

7. The medical connector of claim 1 wherein said medical tubing leg includes a friction bump contacting said height compensating foot for restraining movement of said height compensating foot about said medical tubing leg.

8. The medical connector of claim 1 wherein said height compensating foot is rotatable about said second axis.

9. The medical connector of claim 8 wherein said height compensating foot includes a detent for indexing said height compensating foot in set positions around said tubing leg.

10. The medical connector of claim 1 wherein said height compensating foot raises said angular bend of said connector body to position said catheter leg at an angle of incline relative to a support surface.

11. The medical connector of claim 10 wherein said angle of incline is between 5 and 30 degrees.

12. The medical connector of claim 1 wherein said medical tubing leg has an annular portion with an outer surface adjacent said second end portion; and
   said collar is sized to rotatably fit around said outer surface of said annular portion.

13. The medical connector of claim 12 wherein said outer surface is one of a recessed and raised surface.

14. The medical connector of claim 12 wherein said foot support member projects away from said collar to form an acute angle relative to said second axis.

15. The medical connector of claim 14 wherein said height compensating foot projects away from said collar toward said angular bend.

16. The medical connector of claim 14 wherein said height compensating foot projects away from said collar toward said second end portion.

17. A medical connector for connecting medical tubing and a catheter inserted into a patient, the connector comprising:
   a connector body having:
      an elongated hollow catheter leg having a first end portion adapted to detachably connect to said catheter and a first axis extending centrally through said hollow portion of said catheter leg;
      an elongated hollow medical tubing leg having a second end portion adapted to connect to said medical tubing and an annular portion with a recessed outer surface adjacent said second end portion, said medical tubing leg also having a second axis extending centrally through said hollow portion of said tubing leg; and
      an angular bend intermediate said catheter leg and medical tubing leg wherein said first and second axes intersect; and
   a height compensating foot extending from a collar sized to rotatably fit around said outer surface of said annular portion, and being a cantilevered member extending from said collar.

18. The medical connector of claim 17 wherein said foot support member projects from said collar to form an acute angle relative to said second axis.

19. The medical connector of claim 17 wherein said collar is hollow and circular.

20. The medical connector of claim 17 wherein said collar is a split collar.

* * * * *